(12) United States Patent
Banks (10) Patent No.: US 7,871,444 B2
(45) Date of Patent: *Jan. 18, 2011

(54) METHOD OF TESTING FOR ATP LOAD IN COMMERCIAL LAUNDRY AND FOR DATA TRACKING THE RESULTS

(75) Inventor: Allen G. Banks, Franklin, OH (US)

(73) Assignee: Washing Systems, LLC, Cincinnati, OH (US)

( * ) Notice: Subject to any disclaimer, the term of this patent is extended or adjusted under 35 U.S.C. 154(b) by 325 days.

This patent is subject to a terminal disclaimer.

(21) Appl. No.: 12/015,797

(22) Filed: Jan. 17, 2008

(65) Prior Publication Data

US 2008/0176260 A1    Jul. 24, 2008

Related U.S. Application Data

(63) Continuation-in-part of application No. 11/656,054, filed on Jan. 22, 2007, now Pat. No. 7,628,823.

(51) Int. Cl.
*C11D 3/00*     (2006.01)
*B08B 7/04*     (2006.01)
*C12Q 1/66*     (2006.01)

(52) U.S. Cl. .................................. 8/137; 134/10; 435/8
(58) Field of Classification Search ....................... 8/137, 8/137.5; 134/10; 435/8
See application file for complete search history.

(56) References Cited

U.S. PATENT DOCUMENTS

| | | | |
|---|---|---|---|
| 2,165,884 A * | 7/1939 | Chamberlin et al. ............ 8/159 |
| 4,385,113 A | 5/1983 | Chapelle et al. | |
| 4,467,530 A * | 8/1984 | Fesmire et al. ................. 34/313 |
| 5,004,684 A | 4/1991 | Simpson et al. | |
| 5,811,251 A | 9/1998 | Hirose et al. | |
| 5,905,029 A | 5/1999 | Andreotti et al. | |
| 5,965,453 A * | 10/1999 | Skiffington et al. .......... 436/165 |
| 6,180,395 B1 | 1/2001 | Skiffington et al. | |
| 6,653,147 B2 | 11/2003 | DiCesare | |
| 7,132,249 B1 | 11/2006 | Salter et al. | |
| 2005/0070701 A1 | 3/2005 | Hochstetler et al. | |
| 2006/0010611 A1 | 1/2006 | Snow | |
| 2006/0170913 A1 | 8/2006 | Burke et al. | |

FOREIGN PATENT DOCUMENTS

WO    WO 2005093085 A1 *    10/2005

OTHER PUBLICATIONS

McCarthy, Brian. Bioluminescent Assay of Microbial Contamination on Textile Materials. 2001. International Biodeterioration & Biodegration. 79-83.*
Internet Website, Charm Sciences, Inc.—Food Safety Technology http://www.charm.com—WaterGiene™; New Sensitive ATP Indicator for Water Quality Products: WaterGiene™; PocketSwab® Plus—Now with Room Temperature Stability; PocketH2O™—ATP Quality Test for Water; AllerGiene®—An ATP Based Food Cross-Contact Control.
Internet Website, Antimicrobial Specialists & Associates, Inc. (AMSA, Inc.) http://amsainc.com—Welcome to AMSA, Inc.; All-in-One Shot™ ATP Test Pens; Welcome to the World of ATP analysis; How to Interpret ATP Numbers.
Sabina Fijan et al., "Hygiene monitoring of textiles used in the food industry", Brazilian Journal of Microbiology, vol. 37, No. 3, Jul. 2006 (2006-2007), pp. 356-361.
European Supplementary Search Report, dated Mar. 29, 2010.

* cited by examiner

*Primary Examiner*—Lorna M Douyon
*Assistant Examiner*—Tanisha Diggs
(74) *Attorney, Agent, or Firm*—Wood, Herron & Evans, L.L.P.

(57) ABSTRACT

A method of testing for sanitization of textiles comprises the steps of cleaning textiles in a water solution and testing the water solution for the presence of contaminants such as adenosine triphosphate (ATP), typically with a luminometer. Typically, the water solution will be drained from a cleaning vessel and tested. Another option is the testing of the water solution extracted after draining such as by a spin cycle. The method provides improved accuracy of test results as to the level of cleanliness. In addition, testing at this early step of the laundering process allows for additional cleaning if needed without having undertaken costly and time-consuming steps such as drying. Moreover, absent re-contamination of the textiles after the cleaning process, drying and finishing procedures may be accomplished without further sanitizing the textiles.

8 Claims, 6 Drawing Sheets

METHOD OF TESTING FOR ATP LOAD IN COMMERCIAL LAUNDRY AND FOR DATA TRACKING THE RESULTS

CROSS REFERENCE TO RELATED APPLICATION

This application is a continuation in part of nonprovisional U.S. patent application Ser. No. 11/656,054, filed Jan. 22, 2007 now U.S. Pat. No. 7,628,823; the disclosure of which is incorporated herein by reference.

BACKGROUND OF THE INVENTION

1. Technical Field

The present invention relates generally to the laundering of textiles. More particularly, the invention relates to the insurance of an acceptable level of cleanliness of the textiles. Specifically, the invention relates to the testing of the water solution in which the textiles are cleaned for the presence of adenosine triphosphate (ATP).

2. Background Information

In the field of industrial laundering, there is a need to ensure that textiles which are laundered meet certain standards of cleanliness. Of particular concern is the amount of bacteria on the laundered textiles although the amount of other contaminants is also important. Testing for the presence of adenosine triphosphate (ATP) is a useful indicator of various contaminants including bacteria because ATP delivers energy to all living organisms and is found in organisms both living and dead.

One of the current primary test methods involves the direct testing of textiles which have been laundered and dried. In particular, test procedures have been developed which utilize a swab rubbed directly on textiles in order to obtain a test sample of ATP therefrom. A luminometer is then used to quickly analyze the concentration or amount of ATP on the swab. A test kit using such a swab is described in greater detail in U.S. Pat. No. 6,180,395 granted to Skiffington et al., which is incorporated herein by reference. This test method provides rapid results and thus is a great advantage over the relatively slow process of bacterial colony growth, which usually takes about two days and is obviously not suitable for the purposes of testing laundered textiles.

While such swabbing methods are very convenient, they nonetheless have some drawbacks. One disadvantage is that the testing occurs after the textiles have been dried. Thus, if a given piece or batch of textiles must be re-washed due to an unacceptable ATP level which remained after laundering, that piece or batch of textiles will have already undergone the costly and time consuming step of drying. In addition, the swab testing of a given textile may produce different results depending on where the textile is swabbed. More particularly, a given textile may have been heavily soiled in one area and lightly soiled in another area so that even after laundering, the area which was heavily soiled may retain a greater degree of contamination. In addition, in order to obtain a suitable sample size which is likely to be representative of a large batch of textiles, a fairly large number of textiles must be individually tested in the present swabbing method to minimize concerns related to random sampling. Thus, there is a need in the art to provide a test for sanitation of textiles at an earlier stage of the laundering process while minimizing the number of tests performed.

BRIEF SUMMARY OF THE INVENTION

The present invention provides a method comprising the steps of cleaning textiles with a water solution whereby the water solution becomes used; and testing the used water solution for the presence of adenosine triphosphate (ATP).

DETAILED DESCRIPTION OF THE INVENTION

A first method of the present invention is described with reference to FIGS. 1-2; and a second method is described with reference to FIG. 3. Additional variations of the method of the present invention are described with reference to FIGS. 4-6. Generally, the methods of the present invention are used to ensure the sanitation or cleanliness of laundered textiles or foodware.

Figure 1:
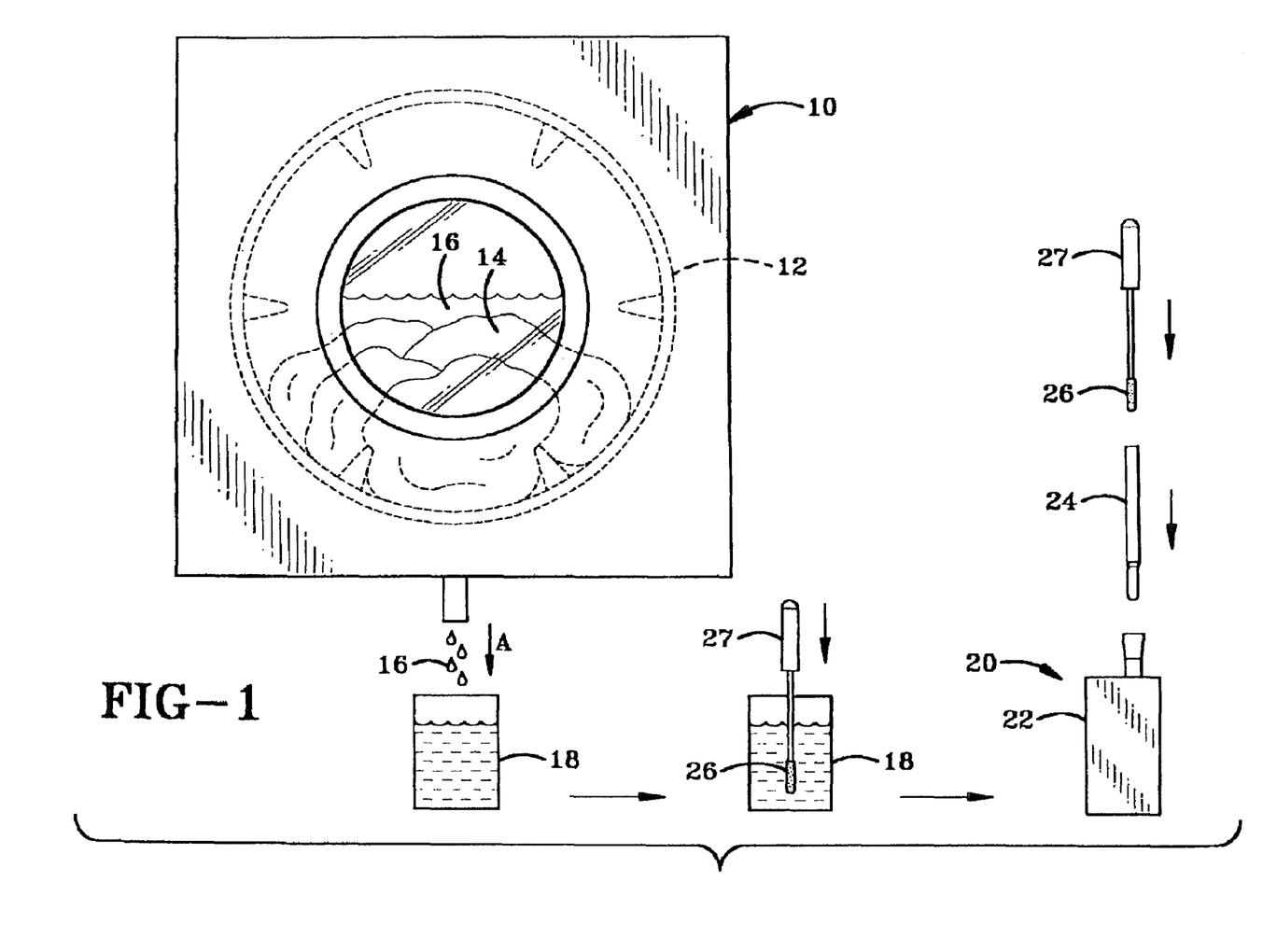
FIG. 1 is a diagrammatic view of a washing machine and a testing device for testing the water solution drained from within the washing machine.
Figure 2:
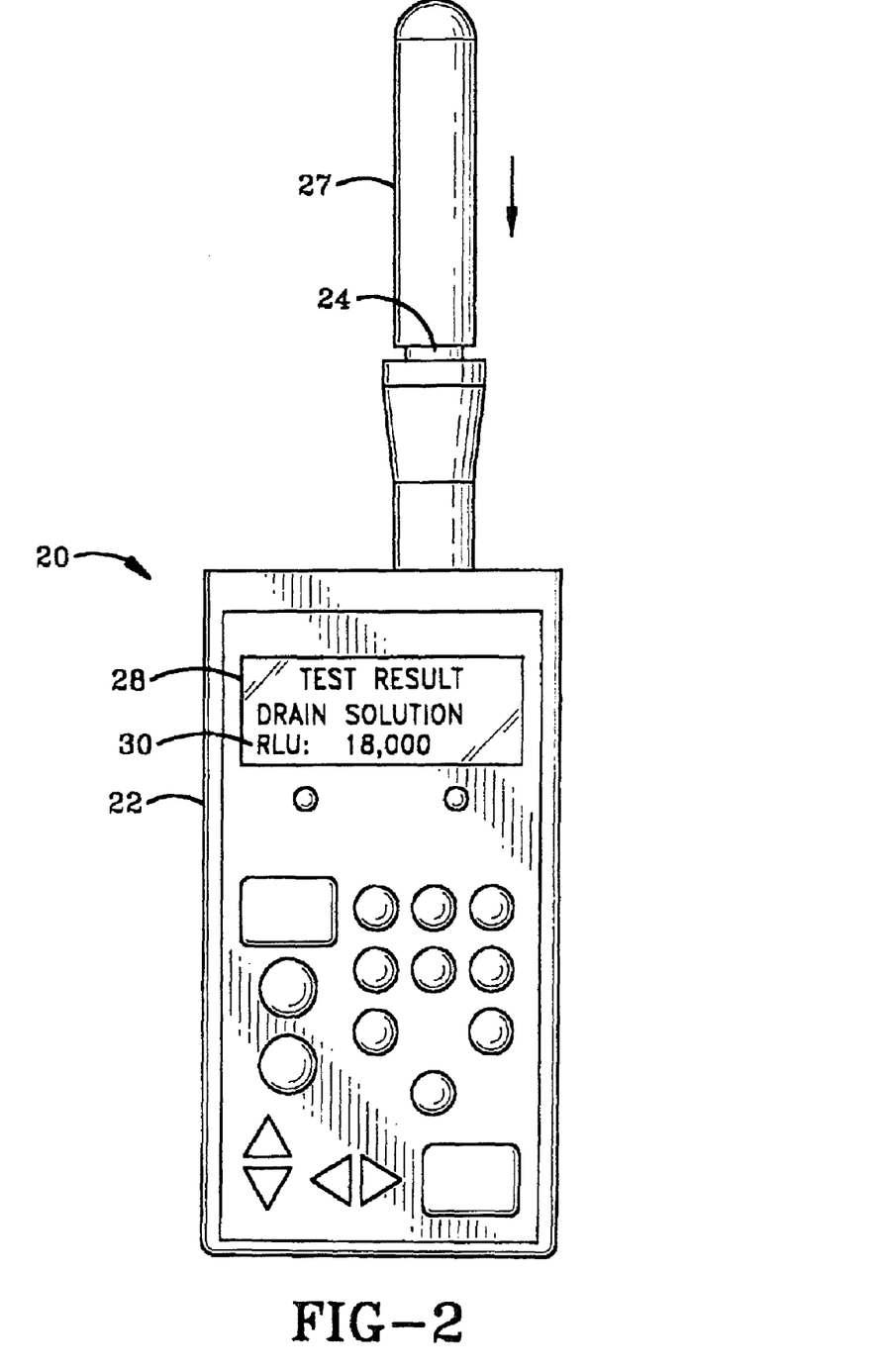
FIG. 2 is a diagrammatic view of the testing device.

FIG. 1 shows a cleaning device in the form of a washing machine or washer 10 having a cleaning vessel in the form of a rotatable drum 12 which defines a washer compartment therein in which laundry or textiles 14 may be placed for washing in a water solution 16 which may contain various detergents, soaps, bleaches and/or other chemicals suitable to promote the cleaning of textiles 14. Textiles 14 may be made up of various textiles such as aprons, butcher coats, sheets, towels, surgical garments, napkins, various other types of uniforms, linens, and so forth. A container or catch vessel 18 is disposed below washer 10 to catch the soiled or dirty water solution 16 which is drained (arrow A) from washer 10 subsequent to the washing or laundering of textiles 14. Vessel 18 is initially free of adenosine triphosphate (ATP) prior to catching the soiled water solution 16, commonly known as sour drain.

Washing textiles 14 in washer 10 is not the only method or device for cleaning textiles 14, and the process shown in the figures is meant to represent the cleaning of textiles by any method using a water solution. For example, dry cleaning utilizes a water solution having dry cleaning chemicals therein to achieve the cleaning process. The present test method may be used to test the used water solution from the dry cleaning process as well. In addition, newly manufactured textiles are typically cleaned by dipping them in a cleaning solution at the manufacturing textile mill. At least the final solution used in this cleaning process involves a water solution which may also be tested by the present method.

An ATP tester 20 is used to test the drained solution 16. In the exemplary embodiment, tester 20 includes a luminometer 22, a sample cylinder 24 and a swab 26 which is removably insertable into cylinder 24 and held by handle 27. Depending on the specific test, the cylinder and/or swab may be inserted into the luminometer 22, or, for instance, a portion of cylinder 24 may be inserted into luminometer 22. One such tester is described in the aforementioned U.S. Pat. No. 6,180,395, which as previously mentioned is incorporated herein by reference. Such testing devices are sold by Charm Sciences, Inc. of Maiden, Mass. under the names Pocketswab® Plus, Watergiene® and Allergiene®. Another portable swab-type device used in an ATP bioluminescent test is sold under the name Lightning® by Idexx Laboratories, Inc. of Westbrook, Me.

These swab-type devices typically have a pre-moistened swab for gathering a test sample which is mixed within a tube such as cylinder 24 with a buffer solution and luciferin-luciferase test reagents which provides for bioluminescence which is read by the luminometer in relative light units (RLU). The Pocketswab® device utilizes a buffer to facilitate the rapid release of ATP from any organic source including micro-organisms and a neutralizer buffer for optimizing the luciferin-luciferase reaction.

Various other ATP tests are also available. Other bioluminescent ATP tests include one which is described in "The Handbook of ATP-Hygiene Monitoring" by Bio-Orbit Oy of Turku, Finland; and one known as the Charm ABC Swab Test sold by the above referenced Charm Sciences, Inc.

As further shown in FIG. 1, swab 26 is dipped in or otherwise wetted by the drained water solution 16, reinserted into cylinder 24 and mixed with the appropriate buffer solution and luciferin-luciferase reagents in order to provide the bioluminescence which is then measured by luminometer 22. FIG. 2 shows that luminometer 22 has a display 28 on which is displayed a specific read out or result 30 of the ATP detected from swab 26, measured in RLU's. Once the sample is placed in luminometer 22, it takes only about five seconds to obtain result 30. A predetermined acceptable level of ATP is typically stored within luminometer 22 and compared with result 30 so that luminometer 22 may also display a pass or fail indication.

If the ATP level is below the acceptable predetermined value, textiles 14 are then removed from washer 10 and dried in a dryer typically heated by a gas or electric heat source. This may be followed by various finishing steps, such as ironing, pressing, steaming such as through a steam tunnel, and the hanging of textiles such as garments on hangers and enclosure of the textiles within bags, boxes or the like. Preferably, no additional sanitizing steps are required after removing the textiles from the washer, as detailed further below.

However, if the ATP level is greater than the acceptable value, textiles 14 will be re-washed or otherwise additionally cleaned and retested in the same manner until the test result is within an acceptable range. Typically, textiles 14 go through multiple cleaning or washing cycles which include washing, draining, rinsing and possibly extraction by centrifuge or the spinning of drum 12 at relatively high speeds. Based on previous testing and general knowledge within the field, personnel within the field of laundering may already know that for a given type of textiles, it will take a certain number of washes and rinses in order to approach the degree of sanitation desired. Thus, a given load of textiles may be washed and rinsed more than once and often many times before the drain water solution is tested for ATP. Because the various types of tests used in the present invention are relatively quick, generally taking no more than five or ten minutes and potentially even less, the testing of the drained water solution will normally be done while the textiles remain in the washer. Preferably, the testing period takes no more than 15 minutes from the time a sample of the used water solution is taken.

Figure 3:
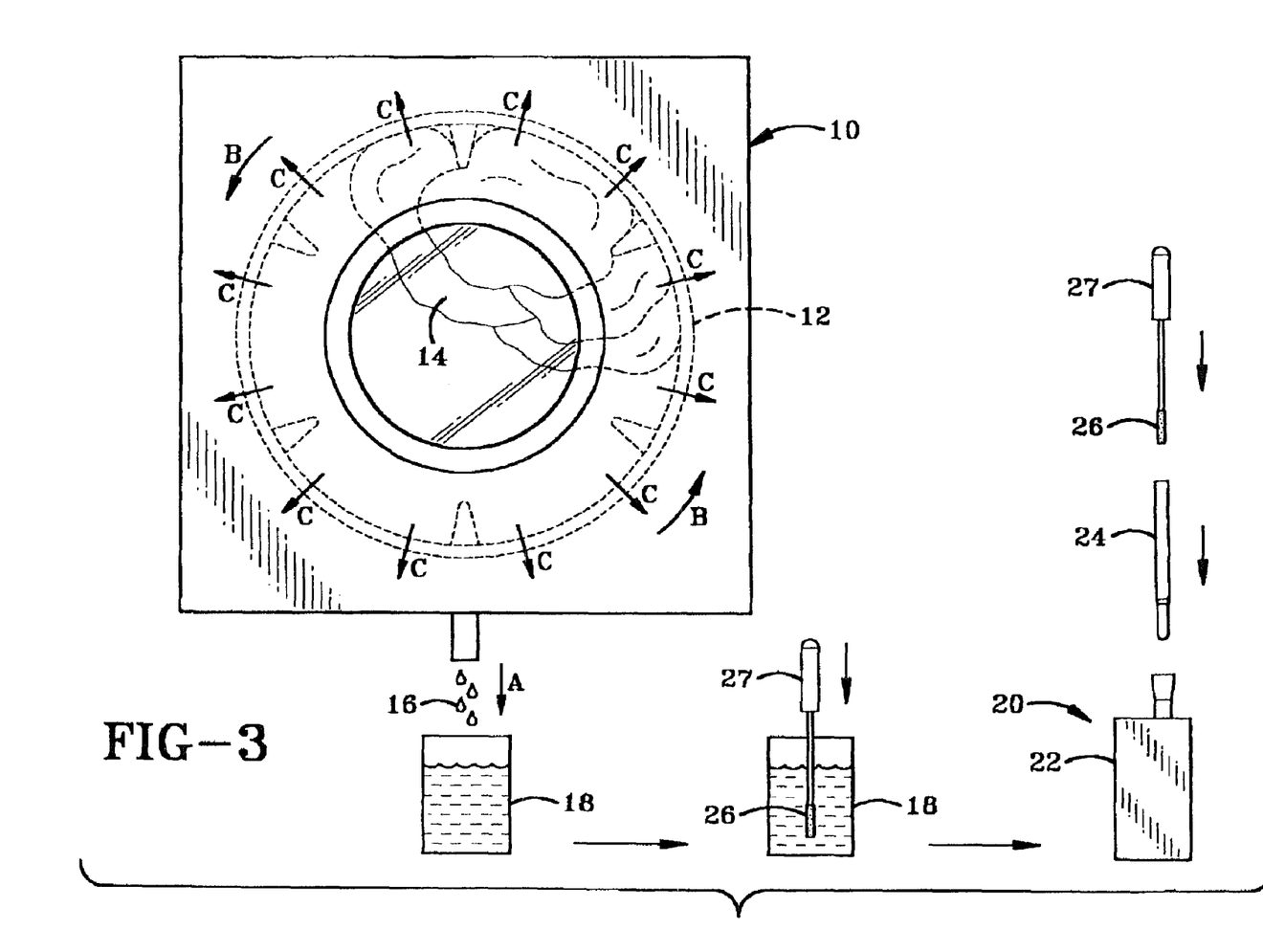
FIG. 3 is similar to FIG. 1 and shows additional water solution being extracted from the drained textiles and the testing of the extracted water solution.

Referring to FIG. 3, the second method of testing is described. The second method is very similar to the first method except that the water solution which is tested is that which is extracted from textiles 14 after the standard drain of solution 16 by gravity and/or pumping thereof. More particularly, drum 12 goes through a spinning cycle, or is rotated at relatively high speeds in order to extract additional water solution 16 from textiles 14 via a centrifuge effect or centrifugal force. Rotation of drum 12 is shown at arrows B and the extracted solution is indicated at arrow C. The extracted solution 16 is then drained into vessel 18 and tested in the same manner as described above. Although extraction of the solution is most typically done by centrifuge, a mechanical press for applying pressure to textiles 14 to press or squeeze the water solution therefrom may also be used.

TABLE 1

Comparison of Test Locations

| Test Location | Dry Soiled Textile | Test Vessel | Washer Drain |
|---|---|---|---|
| ATP (RLU) | 173,387 | 835,793 | 5,444,266 |
| Hach Test Kit (CFU) | <100 | 100,000 | 1,000,000 |

Table 1 Notes:
1. The "dry soiled textile" test was performed prior to being washed; the "test vessel" test was of soiled water solution extracted from a textile which was placed in a water solution in a vessel and stirred or slightly agitated; and the "washer drain" test was a test of soiled water solution drained from the washer in which the textile was washed, the latter being indicative of a high degree of agitation.
2. All ATP results from a swab method with readings from a NovaLum ® luminometer.
3. Hach Test Kit readings were taken after 48 hours of bacterial growth and reported as colony-forming units (CFU). In particular, the tests were done with a Hach Paddle Tester, Total Aerobic Bacteria/Disinfection Control Test Kit sold by the Hach Company of Loveland, CO.

Table 1 primarily shows that the test of the dry soiled textile is generally inaccurate and thus may be misleading. As will be appreciated, even when the test of the dry textile is performed with a pre-moistened swab, the testing of the textile directly, especially when dry, is essentially a surface test which will not indicate the level of ATP or various contaminants further entrapped within the fibers of the cloth. The "test vessel" test shows that even a small degree of agitation of the dirty textile in a water solution allows various contaminants to be released or extracted therefrom to a notably greater degree than possible from the swabbing of the dry soiled textile. The soiled washer drain solution shows a far greater amount of ATP which is in keeping with the ability of the high-agitation washer to strip all sorts of contaminants from the fabric via mechanical action, solubility in water and/or the entrainment of the contaminants in the water solution.

The results from the Hach test kit provide a similar comparison. In addition, the test results from the Hach test kit indicate that the dry soiled textile may actually be within an acceptable range of sanitation which would be expected only subsequent to the textile being washed. The results from Table 1 thus emphasize the need for a test which better establishes a more accurate reading of the ATP level in the textiles.

TABLE 2

ATP Test Results of Various Textile Types

| Washer | Max. Capacity (lbs. clean dry cotton) | Textile Type | No. of Steps | Sour Drain Test (RLU) | Wet Textile Test (RLU) |
|---|---|---|---|---|---|
| #1 | 450 | white industrial | 21 | 39624 | 0 |
| #2 | 450 | 65/35 shirts | 17 | 9510 | — |
| #3 | 600 | colored cotton | 15 | 40000 | 0 |
| #4 | 600 | 65/35 pants | 13 | 18034 | 0 |

Table 2 Notes:
1. The term "65/35" stands for 65% polyester and 35% cotton; typically, the white industrial textile type is of a 65/35 blend.
2. The number of steps typically includes a combination of washing, draining, rinsing and spinning in various orders depending on the textile type.
3. Tests performed via Pocketswab ® Plus method with readings provided by a NovaLum ® luminometer.
4. In the sour drain test, the swab was wetted with the soiled water solution drained from the washer after the final step indicated in the number of steps column.
5. In the wet textile test, the swab was rubbed on the wet textile which was still wet with the water solution of the wash after the final step of washing.

As Table 2 shows with reference to the Pocketswab® Plus test, even when the sour drain test gave an ATP reading of 40,000 RLU, the test of the wet textile gave an ATP reading of 0 RLU. This further emphasizes the difficulty of obtaining an accurate result concerning the level of contaminants via the direct swabbing of a textile.

If the textiles are sufficiently clean at the end of the washing or other cleaning process, there is no need, absent any re-contamination of textiles, for additional sanitizing steps thereafter. This is the most preferred condition of the textiles subsequent to washing or other cleaning in order to eliminate these additional sanitizing steps which may be relatively costly. Thus, it is preferred to maintain the textiles in a sanitary condition during the process of drying and all of the finishing steps and delivery to the customer or user of the textiles without additional sanitization.

Applicant's method of ATP testing thus provides a more accurate indicator of the level of ATP and associated bacteria of laundered textiles than do tests based on the direct swabbing of the textile. In addition, the textiles are tested for ATP at an earlier stage of the laundering process which can avoid the unnecessary repetition of various steps of the laundering process. Moreover, the present method may eliminate the need for sanitizing procedures subsequent to the washing or other cleaning process while maintaining a level of sanitation equal to or better than that of the prior art methods.

Figure 4:
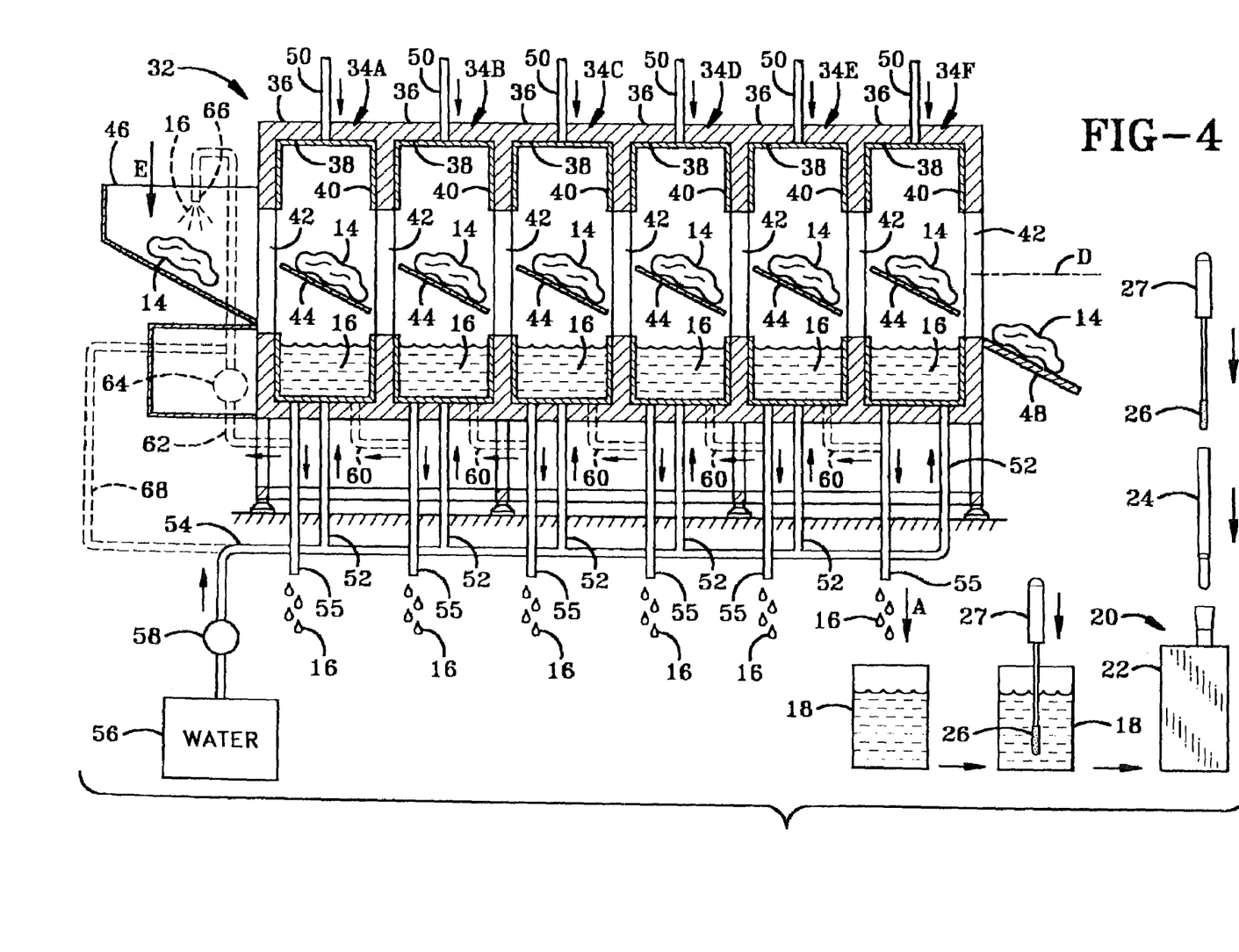
FIG. 4 is a diagrammatic side view of a tunnel washer and the testing device for testing the water solution drained therefrom.

By way of further example, the present testing method may also be used to test for contamination of textiles which were laundered in a tunnel washer 32 (FIG. 4). Tunnel washers are well known in the art and include multiple modules such as shown at 34A-F which communicate with one another for the serial washing of textiles 14. Each module 34 includes its own housing 36 which is connected to the adjacent housing 36 and defines a water containing chamber 38 in which a cleaning vessel in the form of a drum 40 is disposed and rotatable about a horizontal axis D extending along the length of tunnel washer 32. Through openings 42 are formed on either side of each housing 36 and each drum 40 to provide entry and exit openings between the various modules 34 so that each module communicates with one another to allow textiles 14 to pass therebetween. More particularly, each module 34 includes a transfer chute 44 to facilitate transfer of textiles 14 from a given module 34 to a module 34 downstream thereof. Washer 32 includes a feed chute 46 at its upstream end which communicates with module 34A via the first opening 42. Washer 32 further includes a discharge chute 48 at its downstream end which communicates with module 34F via the respective opening 42. Each module 34 is shown as having a detergent or soap inlet 50 which communicates with the respective chamber 38 for feeding into chamber 38 soap, detergent, bleach or other suitable components used to facilitate the cleaning of textiles 14 during the laundering process. Many tunnel washers 32 may only include a soap feed line such as line 50 in the more upstream modules 34A-C without using such feed lines for the other modules in that the more downstream modules may be used simply to provide a greater degree of rinsing without additional washing with soap or the like. Each module also includes a water feed line 52 which communicates with the respective chamber 38 and with a main water line 54 which is in communication with a source 56 of water via a pump or valve 58. Washer 32 may also include transfer lines 60 which provide fluid communication between the chambers 38 of adjacent modules 34. An additional transfer line 62 may communicate with the upstream chamber 38 and a pump 64 with an exit end 66 above feed chute 46. An additional water feed line 68 may communicate with source 56 of water to provide water above feed chute 46 at exit end 66 or the like.

In operation, textiles 14 are placed into feed chute 46 as indicated at Arrow E so that textiles 14 may be fed through the first opening 42 into chamber 38 of first module 34A. Clean water from source 56 will then flow via pump or valve 58 and the respective feed line 52 into chamber 38 of module 34A. Typically, soap, detergent, bleach or other suitable cleaning agents will be fed into chamber 38 of first module 34A via its feed line 50. The clean water and cleaning agents will form the water solution 16 within chamber 38 of module 34A. Optionally, clean water from source 56 may flow through line 68 and/or 62 and out of exit end 66 to wet textiles 14 while in feed chute 46. Alternately, water solution 16 from within chamber 38 of first module 34A may be fed through transfer line 62 and pumped via pump 64 to exit end 66 to likewise wet textiles 14 while in feed chute 46. Once textiles 14 are disposed in drum 40 of module 34A, an electronic control unit is programmed to rotate drum 40 back and forth in oscillating manner in order to provide the agitation to wash textiles 14 within solution 16. Depending on the program, the cleaning cycle for module 34A may include a washing cycle, a washing and rinse cycle, or several washing and rinse cycles. At the end of the one or more washing and rinsing cycles for module 34A, drum 40 will be rotated a larger degree as known in the art in order to move textiles 14 from within drum 40 onto the respective transfer chute 44 to facilitate the movement of textiles 14 from module 34A to module 34B via the opening 42 therebetween. This mode of transfer is used between each of the respective modules 34 at the appropriate time. In general, textiles 14 will continue through the various wash and/or rinse cycles within each module 34A-F in a serial fashion until discharged at the downstream end via discharge chute 48. Tunnel washer 32 may thus be programmed for feeding fresh water into each chamber 38 as desired before a given wash or rinse cycle. Alternately, water may be fed from source 56 through main line 54 and the feed line 52 of module 34F and subsequently upstream to each of chambers 38 via transfer lines 60 so that the cleanest water is in module 34F with the dirtiest water in module 34A with varying degrees of contamination in the modules therebetween, getting generally more contaminated as the water moves upstream toward module 34A. This latter method utilizes the water more than once by feeding into each chamber 38. Regardless of the particular program utilized, water solution 16 will eventually be drained from the respective chambers 38 via drain lines 56 or transfer line 62 at exit opening 66. The drained or used water solution 16 is presented as droplets exiting from each of drain lines 56 and dashed lines extending from exit opening 66.

Testing of the used water solution 16 is typically performed on the water solution from module 34F although the testing may be performed on the water solution drained from any of chambers 34. FIG. 4 thus shows water solution 16 being drained (Arrows A) into catch vessel 18 to be tested via swab 26 and tester 20 as described earlier herein.

Figure 5:
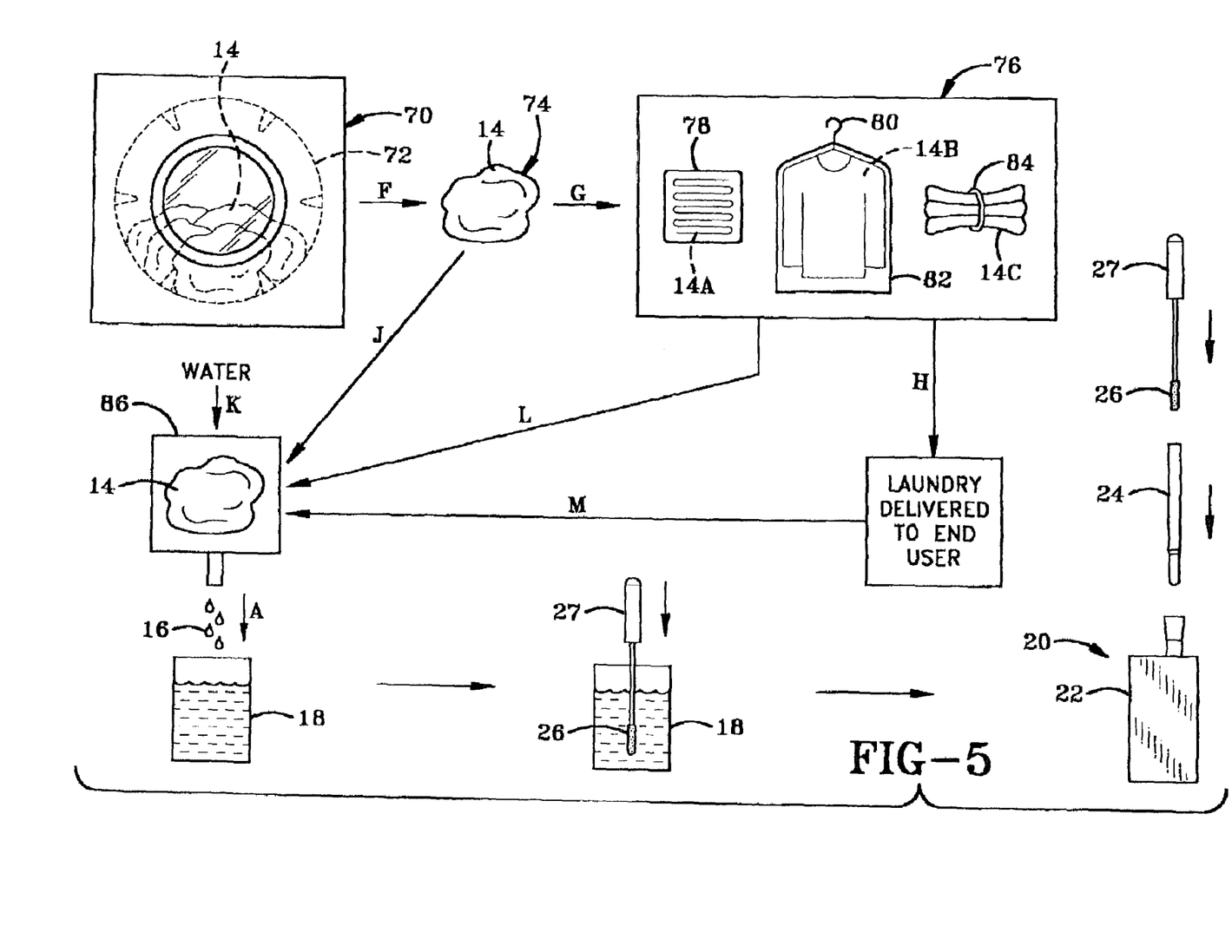
FIG. 5 is a diagrammatic flowchart showing washed textiles being dried in a dryer and tested with the method of the present invention subsequent to drying.

Referring now to FIG. 5, the testing method of the present invention may also be used subsequent to the drying of textiles 14 at any point during the processing of the laundered textiles. More particularly, the laundered textiles from one of washers 10 or 32 will be transferred into a dryer 70 having a housing with a drum 72 rotatably mounted therein for receiving textiles 14 to be dried. Subsequent to drying, the batch of textiles 14 is removed from dryer 70 as shown in Arrow F to produce a dried batch 74 of textiles 14. The textiles 14 of batch 74 will then undergo what is typically referred to in the industry as the "wrapping out" process as indicated at Arrow G to produce a batch 76 of wrapped out textiles 14A-C. The wrapped out textiles are then delivered (Arrow H) to the end user. The wrapping out process may include various procedures depending on the type of textile. Batch 76 for instance includes folded textiles 14A such as bed linens or table linens which are folded and then put into a container typically by wrapping with cellophane or other plastic sheet material 78. Batch 76 may also include hanging textiles 14B typically in the form of shirts or pants which are hung on a hanger 80 and then enclosed in a container 82 typically in the form of a sheet of wrapping material most typically in the form of a cellophane or other plastic sheet material although paper may be used as well. Containers 78 and 82 may also include the use of boxes. Batch 76 may also include the use of such textiles as bar towels 14C or the like which may simply be banded together by a rubber band 84 or the like without being wrapped in the plastic material.

Because there is a chance of recontamination of the laundered textiles subsequent to the washing and drying procedures, the testing method of the present invention may be used at any stage of the process. Thus, one or more textiles 14 of dried batch 74 may be removed from the batch as indicated at Arrow J so that water may be added to the removed textiles 14 as indicted at Arrow K to facilitate the testing process. The wetted textiles 14 will then be placed in a water extraction device 86 to produce the extracted water solution 16 which is once again caught in the vessel 18 as indicated by Arrow A in FIG. 5. Extraction device 86 may be a centrifuge or a press or any suitable mechanism for the purpose. Solution 16 is tested in the same manner as previously described as shown in FIG. 5. The testing may also occur subsequent to the wrapping out process. Thus, one or more of textiles 14A-C may be removed from batch 76 subsequent to the particular wrapping out procedure as shown at Arrow L to be tested in the same manner by adding water as shown at Arrow K and extracting the solution therefrom. Similarly, textiles 14 may be handled in the same manner subsequent to being delivered to the end user as indicated at Arrow M. During the testing process of batches 74 or 76 or even subsequent to delivery to the end user, if the tested textiles 14 prove to be contaminated beyond an acceptable level, the ATP testing may be utilized again for additional textiles 14 within a given batch of laundry to determine whether the contamination of a given textile 14 is an isolated incident or is a more general problem. In either case, the textiles which are determined to be outside the acceptable level can then be re-washed as needed to provide an acceptable level of cleanliness.

Figure 6:
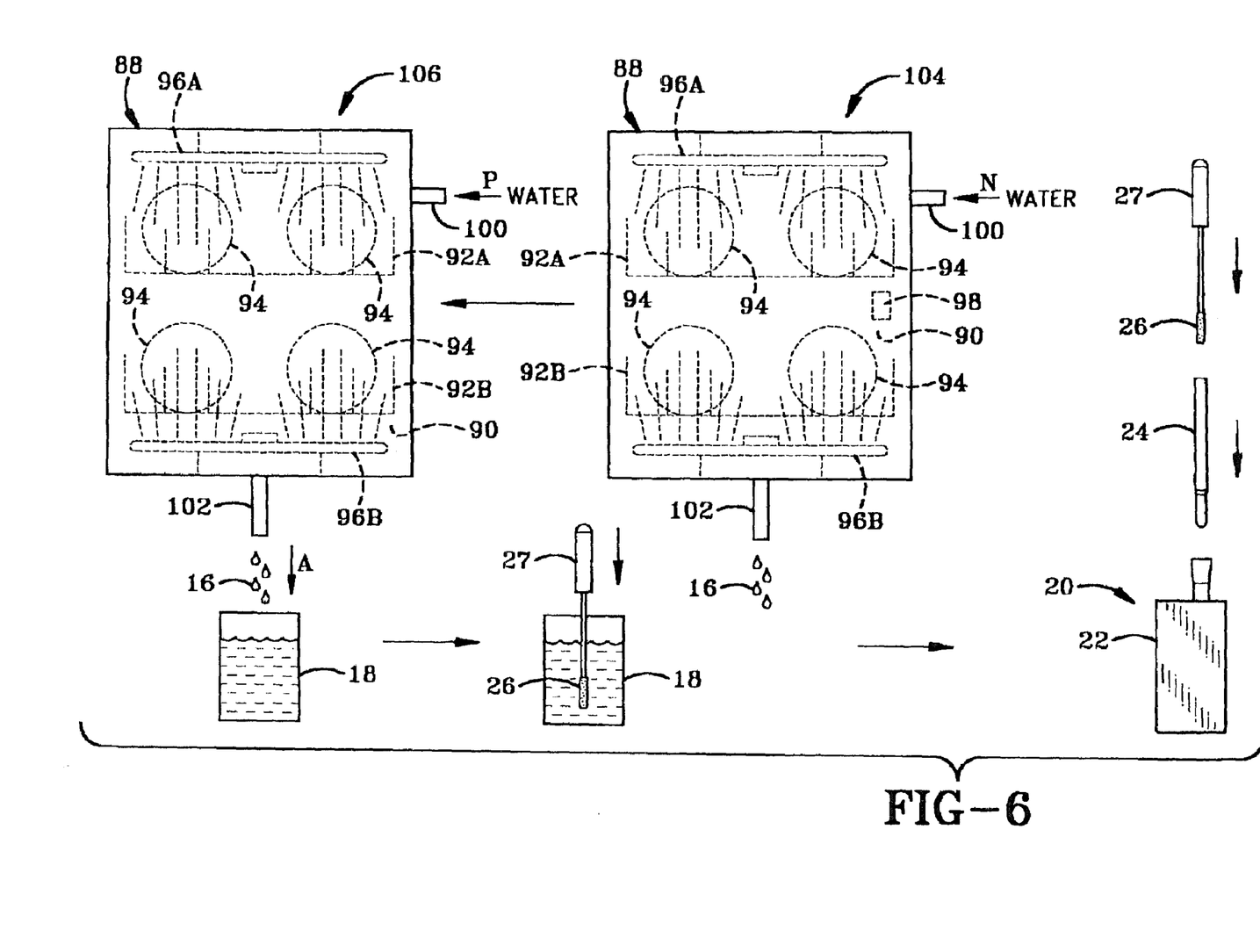
FIG. 6 is a diagrammatic flowchart showing dishes being washed in a dishwasher and the drained water solution therefrom being tested by the present method.

Referring now to FIG. 6, the present testing method may also be used when testing for the level of contamination of dishwasher drain water. Most typically, the process would be used with an automated dishwasher 88 of any type. Generally, dishwater 88 includes a housing defining an interior wash chamber 90 in which a plurality of racks such as upper and lower racks 92A and 92B are disposed for supporting various foodware 94 adjacent respective sprayers 96A and B for respectively forcefully spraying water on foodware 94 for cleaning said foodware. Foodware 94 typically includes dishware such as plates and bowls, cookware such as pots and pans, and silverware or cooking and eating utensils such as forks, knives and spoons. A detergent 98 is typically utilized to facilitate the cleaning process. Dishwasher 88 includes a water inlet 100 in communication with sprayers 96 and an outlet or drain 102 in communication with interior chamber 90. FIG. 6 illustrates at numeral 104 a washing cycle or cycles and at numeral 106 a rinsing cycle or cycles 106. Thus, water moves through inlet 100 into sprayers 96 to spray water onto dishware 94 utilizing detergent 98 to facilitate cleaning of dishware 94. After one or more washing cycles 104, the water solution within interior chamber 90 is drained through drain 102. Subsequently, water is moved through inlet 100 as indicated at Arrow P to facilitate the rinsing cycle 106 in which the water is again sprayed through sprayers 96 without the use of soap or detergent 98. The rinsing water solution is then drained from interior chamber 90 through drain pipe 102 and caught within vessel 18 so that the test of the present invention may be performed as previously described. The test may also be performed on the water solution 16 which is drained from the washing cycle 104 instead of the rinsing cycle 106. However, the test for cleanliness of dishware 94 is most typically after the rinse cycle 106. As with the washing of textiles, if the test should read above a predetermined level, dishware 94 may be washed and rinsed again until the drained solution when tested meets the cleanliness standard desired.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A method of laundering textiles comprising the steps of:
   cleaning textiles with a water solution whereby the water solution becomes used in a first cleaning step;
   cleaning said textiles with water in one or more subsequent cleaning steps and generating used water; and
   testing the used water from at least one of said subsequent cleaning steps for the presence of adenosine triphosphate (ATP) to thereby ensure a level of cleanliness of said textiles, wherein the one or more subsequent cleaning steps comprise the step of cleaning textiles with water in a cleaning vessel whereby the water becomes used; further comprising the steps of draining the used water from the cleaning vessel; and wherein the step of testing comprises the step of testing the drained water.

2. The method of claim 1 wherein the step of testing comprises the step of assaying the used water for the presence of ATP by mixing the used water with luciferase and luciferin.

3. The method of claim 1 wherein the step of testing comprises the step of assaying the used water for the presence of ATP by mixing the used water with a buffer which accelerates the release of ATP.

4. The method of claim 1 wherein the step of testing comprises the step of testing the used water for the presence of ATP with a luminometer.

5. The method claimed in claim 1 wherein said first cleaning step and said one or more subsequent cleaning steps are conducted in a tunnel washer.

6. The method claimed in claim 5 wherein the used water tested for the presence of adenosine triphosphate is collected from a final section of said tunnel washer.

7. The method claimed in claim 1 wherein in said one or more subsequent cleaning steps a detergent is dissolved in said water.

8. A method of laundering textiles comprising the steps of:
cleaning textiles with a water solution whereby the water solution becomes used in a first cleaning step;
cleaning said textiles with water in one or more subsequent cleaning steps and generating used water;
testing the used water from at least one of said subsequent cleaning steps for the presence of adenosine triphosphate (ATP) to thereby ensure a level of cleanliness of said textiles;
wherein the one or more subsequent cleaning steps comprise cleaning textiles with water in a cleaning vessel whereby the water becomes used; further comprising the steps of draining the used water by force of gravity from the cleaning vessel; and extracting a further amount of the used water from the drained textiles; and wherein the step of testing comprises the step of testing the extracted water.

* * * * *